United States Patent

McRae et al.

[11] Patent Number: 4,980,571
[45] Date of Patent: Dec. 25, 1990

[54] METHODS AND APPARATUS FOR MEASURING SIDESTREAM SMOKE

[75] Inventors: Douglas D. McRae, Chesterfield; Bobby W. Francis, Mechanicsville; Leonard E. Brown, Jr., Prince George; Roger A. Comes, Midlothian; Randall K. Greene, Richmond, all of Va.

[73] Assignee: Philip Morris Incorporated, New York, N.Y.

[21] Appl. No.: 410,933

[22] Filed: Sep. 22, 1989

[51] Int. Cl.$^5$ .............................................. G01N 21/00
[52] U.S. Cl. .................................... 250/573; 356/439
[58] Field of Search ........................ 250/573; 340/630; 356/437, 438, 439, 440, 433, 434, 338, 337

[56] References Cited

U.S. PATENT DOCUMENTS

| | | | |
|---|---|---|---|
| 1,848,874 | 3/1932 | Fitzgerald | 356/432 |
| 2,034,281 | 3/1936 | Buchholz | 347/518 |
| 2,620,385 | 12/1952 | Grant | 177/311 |
| 2,966,092 | 12/1960 | Hartridge | 88/14 |
| 3,204,449 | 9/1965 | Fordyce | 73/38 |
| 3,207,026 | 9/1965 | Churchill | 88/14 |
| 3,544,218 | 12/1970 | Cassidy | 356/36 |
| 3,653,773 | 4/1972 | Childs | 356/207 |
| 3,792,272 | 7/1986 | Harte et al. | 250/343 |
| 3,826,577 | 7/1974 | Irwin | 356/201 |
| 3,833,305 | 9/1974 | Porter et al. | 250/573 |
| 3,860,818 | 1/1975 | Stalder | 250/343 |
| 3,932,137 | 1/1976 | Culpepper, Jr. | 356/439 |
| 4,544,273 | 10/1985 | Berndt | 356/434 |
| 4,589,775 | 5/1986 | Milhous et al. | 356/439 |
| 4,647,780 | 3/1987 | Dunkel | 250/573 |

FOREIGN PATENT DOCUMENTS 1428167 6/1973 Netherlands.

Primary Examiner—David C. Nelms
Assistant Examiner—George Beck
Attorney, Agent, or Firm—Gerard A. deBlasi

[57] ABSTRACT

Methods and apparatus for continuously and instantaneously measuring sidestream smoke are provided. A hood assembly is provided to fit over the ports of a conventional smoking machine. Sidestream smoke produced by test cigarettes is continuously drawn through the hood by an exhaust system. A laser beam is passed through the smoke one or more times before the beam is sensed by a photodiode detector. An electrical signal from the detector, representing the light transmission, is received by a strip recorder or computer system. The transmission measurements are used to calculate the extinction coefficient of the smoke for comparison purposes.

17 Claims, 4 Drawing Sheets

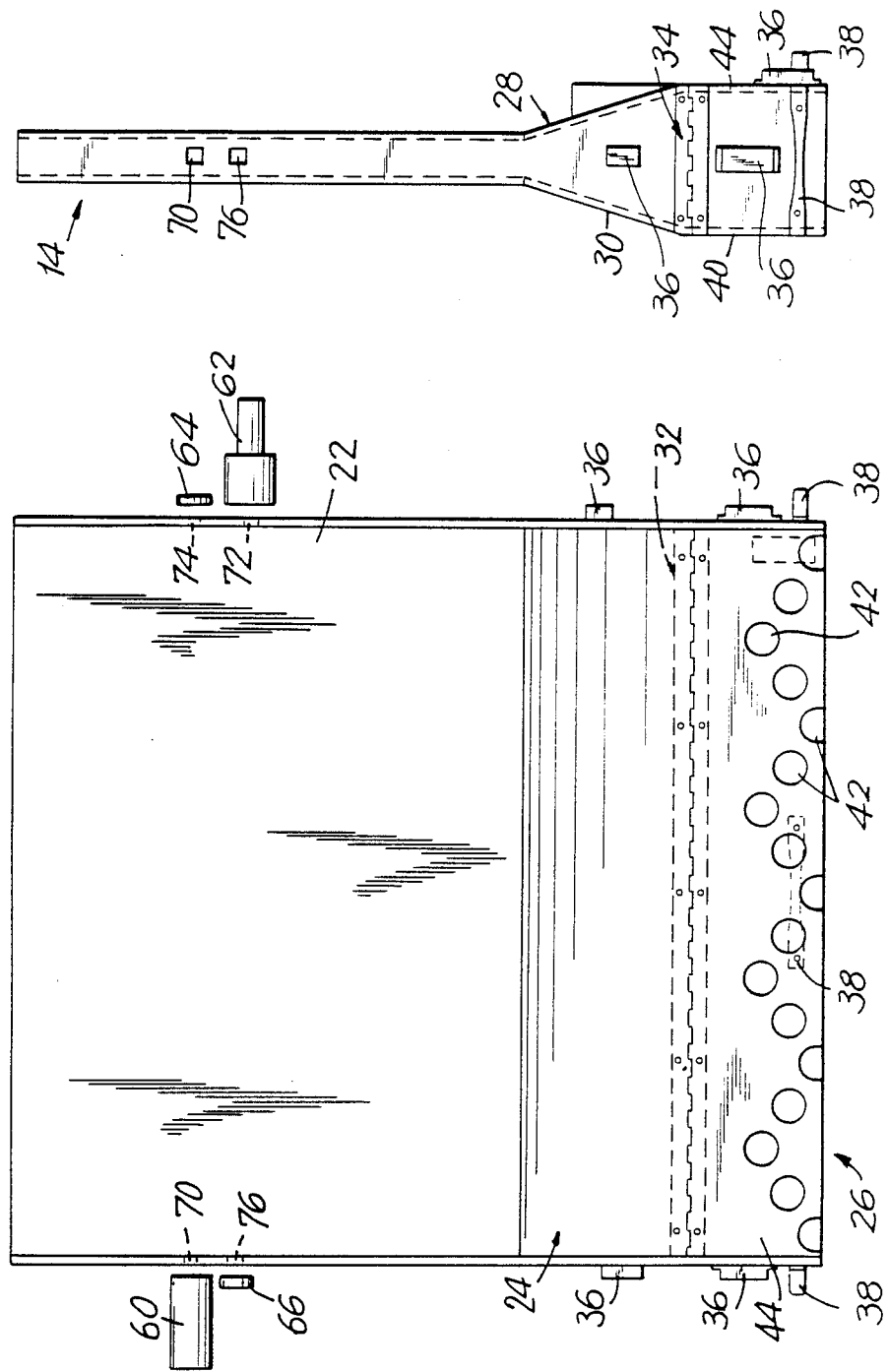

4,980,571

METHODS AND APPARATUS FOR MEASURING SIDESTREAM SMOKE

BACKGROUND OF THE INVENTION

This invention relates to a system for measuring sidestream smoke, and more particularly to a system which continuously and optically senses sidestream smoke drawn past a sensor.

In recent years there has been an increased interest in the amount of sidestream smoke produced by a cigarette. To develop cigarettes which produce less sidestream smoke, it is necessary to develop a system which can quantify the smoke produced by the cigarettes.

One prior attempt to quantify the sidestream smoke produced by cigarettes involved collecting the smoke on Cambridge filters designed to collect mainstream smoke. Once the smoke has been collected, a complex procedure is required to extract, analyze, and weigh the smoke components. Also, this procedure does not permit continuous or instantaneous measurements to be made.

Another attempt to quantify the amount of sidestream smoke produced by cigarettes, described in U.S. Pat. No. 4,589,775, involved accumulating sidestream smoke in a chamber having a sealed top. Light emitted from an LED was transmitted through the accumulated smoke and received by a detector. One drawback associated with accumulating the smoke is the resulting flow of combustibles to the cigarette. The combustible compounds in the smoke may circulate near the cigarette, affecting the cigarette burn, and changing the chemistry and test conditions. Also, this procedure measures the accumulated smoke in the chamber rather than measuring the sidestream smoke produced at any particular instant.

It would be desirable to provide a system for measuring sidestream smoke continuously and instantaneously. It would also be desirable to provide a system which does not affect the burning conditions of the cigarettes under test.

SUMMARY OF THE INVENTION

In view of the foregoing, it is an object of this invention to provide a system for continuously and instantaneously measuring the sidestream smoke produced by cigarettes.

It is a further object of this invention to provide a system for measuring sidestream smoke which does not affect the burn of cigarettes being tested.

It is still another object of this invention to provide a system for measuring sidestream smoke which may be used with commercially available smoking machines.

These and other objects of the invention are accomplished by providing a system for measuring sidestream smoke in which a hood assembly is placed over a conventional smoking machine to channel smoke past an optical system. The optical system includes an illuminating source, such as a laser, and a detector. Light from the source is passed through the smoke one or more times and is sensed by the detector. The reduction in the intensity of light striking the detector is used to quantify the amount of smoke generated by the cigarettes being tested.

The hood assembly is equipped with an exhaust system which draws the smoke from the top of the hood at a predetermined flow rate. The exhaust system prevents smoke from accumulating in the hood, thereby preventing smoke that has passed the optical system from affecting later measurements and from affecting the cigarette burn.

A computer system or strip chart recorder is used to continuously and instantaneously record the test results. Useful results are available without requiring subsequent, complex analyses.

BRIEF DESCRIPTION OF THE DRAWINGS

The above and other objects and advantages of the invention will be apparent upon consideration of the following detailed description, taken in conjunction with the accompanying drawings, in which like reference numerals refer to like parts throughout.

FIG. 2 is a front elevational view of the hood assembly of FIG. 1;

FIG. 3 is a side elevational view of the hood assembly of FIG. 2;

DETAILED DESCRIPTION OF THE PREFERRED EMBODIMENT

Figure 1:
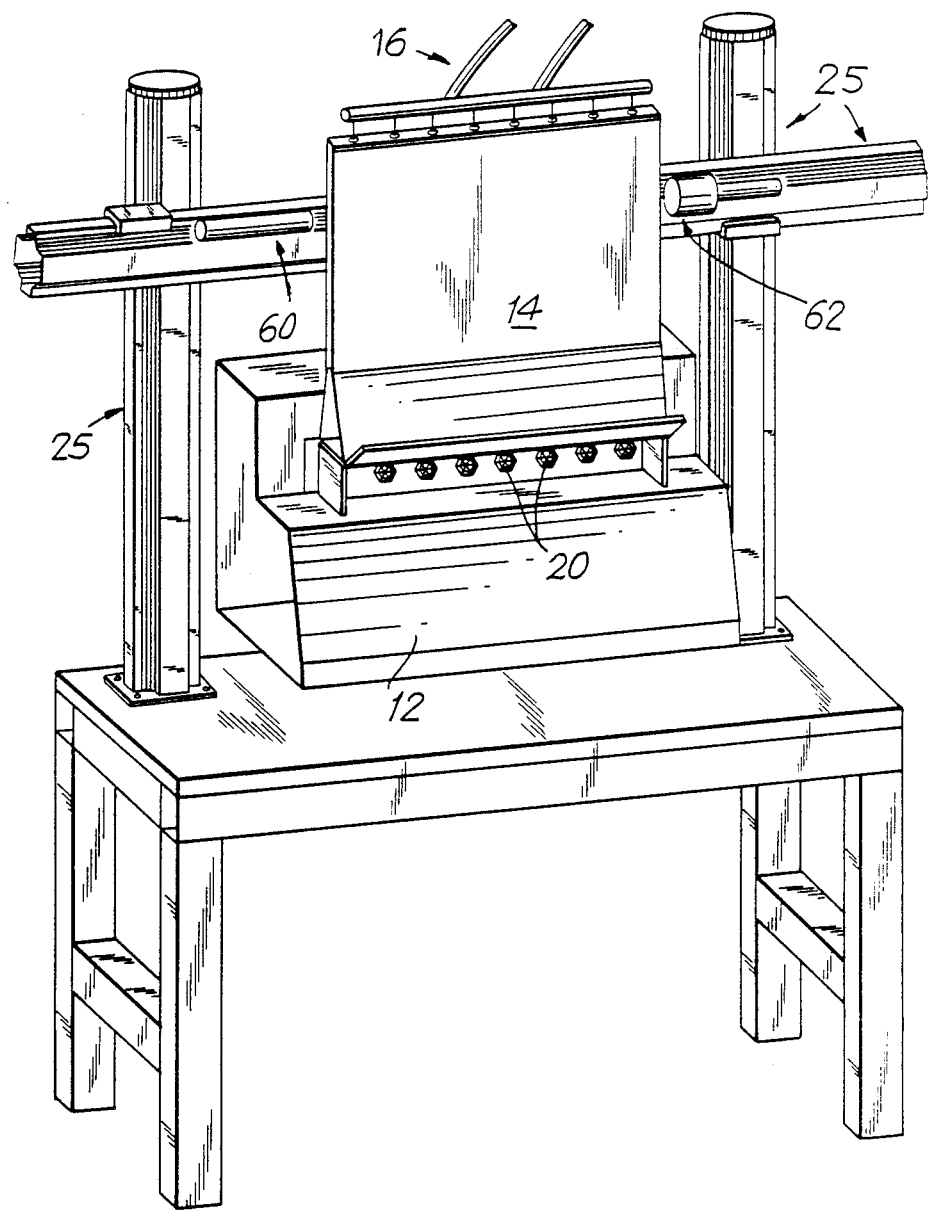
FIG. 1 is a perspective view of the system used to measure sidestream smoke in accordance with the present invention.

Transmission measurements provide a convenient means for measuring the concentration of smoke. The internal calibration point of the initial light intensity (i.e., when no smoke is present) is easily determined and establishes a known reference point for test measurements. The amount of light transmitted through an aerosol is described by the following equation:

$$I = I_0 \exp(-lb_{ext}), \qquad [1]$$

where $I$ and $I_0$ are the intensities of light with and without the smoke being present, respectively, $l$ is the length of the light path, and $b_{ext}$ is the extinction coefficient of the aerosol, which is directly proportional to amount of smoke present. The extinction coefficient is the sum of the scattering coefficient and the absorption coefficient. For cigarette smoke, the absorption coefficient is small and can be neglected. The real part of the refractive index of cigarette smoke, which in part determines the scattering behavior of the smoke, is approximately 1.5 at 514.5 nm. The imaginary part of the refractive index, which determines the absorption behavior of the smoke, has been reported as 0.00133 at 514.5 nm.

The system of the present invention measures the amount of light transmitted through the smoke aerosol. Equation 1 shows that if the light transmitted through the smoke decreases by a factor of two, the amount of smoke is not doubled. The apparatus of the present invention is used to measure the values of $I$ and $I_0$. To determine the concentration of smoke present, $lb_{ext}$ must be calculated using the equation:

$$lb_{ext} = -\ln(I/I_0). \qquad [2]$$

The percent reduction in smoke from an experimental cigarette, relative to a standard, is then calculated using the equation:

$$\% \text{ Reduction in smoke} = 100 \times \frac{(1b_{ext})_{std} - (1b_{ext})_{exp}}{(1b_{ext})_{std}} \quad [3]$$

The path length is a constant and consequently has no effect on the results.

Referring now to the drawings, FIGS. 1-5 show a preferred embodiment of a system for measuring sidestream smoke constructed in accordance with the principles of this invention. The system, designated generally by reference numeral 10, includes a smoking machine 12, a hood assembly 14, an exhaust system 16, and an optical system 18.

Referring to FIG. 1, smoking machine 12 includes several smoking ports 20 for retaining cigarettes or other smoking articles. In the preferred embodiment, machine 12 is an eight port smoking machine, such as the Filtrona Model SM302 smoking machine which is commercially available from Filtrona Instruments and Automation Ltd., Milton Keynes, England. An eight port machine produces a sufficient quantity of sidestream smoke for measurement, yet permits system 10 to remain compact in size. Smoking machine 12 may include an automatic lighting bar for simultaneously and reliably lighting the cigarettes to be tested.

The smoking ports preferably are arranged in a line and compactly spaced approximately 6.25 cm (or 2.5 inches) apart. Smoking machine 12 is a syringe-type machine, which is set to pull approximately 35 cubic centimeters of air per puff. Machine 12 is equipped with disposable Cambridge filter pads, and the cigarettes may be held in place with molded silicon rubber holders.

Hood assembly 14 is designed to contain the sidestream smoke produced by test cigarettes and draw it upward at a substantially continuous flow rate. The dimensions and features of hood assembly 14 will be described for use with the Filtrona smoking machine, but it is understood that one skilled in the art could modify the hood for use with any smoking machine without departing from the scope of this invention.

Referring now to FIGS. 2 and 3, hood assembly 14 includes an upper portion 22, a middle portion 24, and a lower portion 26. Hood assembly 14 may be formed of ¼ inch Lexan (tm) sheets, or any other suitable material, which may be cemented together. Upper portion 22 forms a chamber which typically might be 38.5 cm high by 55 cm across by 2.5 cm deep, having openings at the top for exhausting air and smoke. Lower portion 26, which surrounds smoking ports 20, forms a chamber which typically might be 10.2 cm high by 55 cm across by 10 cm deep. Middle portion 24 connects lower portion 26 to upper portion 22, as shown in FIG. 3. The front and rear panels 28 and 30 forming middle portion 24 are approximately 12.8 cm high, and are angled inward (i.e., toward each other) approximately 16.7 degrees from a vertical position. The overall height of the hood is approximately 61 cm.

Hood assembly 14 is supported by support structure 25. Support structure 25 is a framework constructed from tubular optical benches which are available from Oriel Corp. (Stratford, Connecticut).

The front and side panels of lower portion 26 are hinged along hinge lines 32 and 34, respectively, and may be locked in a raised position by clasps, such as magnetic catches 36, to load and light cigarettes. Handles 38 are provided on the front and side panels of lower portion 26 to facilitate raising and lowering the panels. The rear panel 40 of portion 26 includes a plurality of circular openings 42 (shown in FIG. 2, viewed through the transparent front panel 44) to permit hood assembly 14 to contact smoking machine 12 and to permit smoking ports 20 and string cutoff anchor posts to extend entirely within the hood. The bottom of portion 26 is open to permit air to be drawn into the chamber for combustion.

Figure 4A:
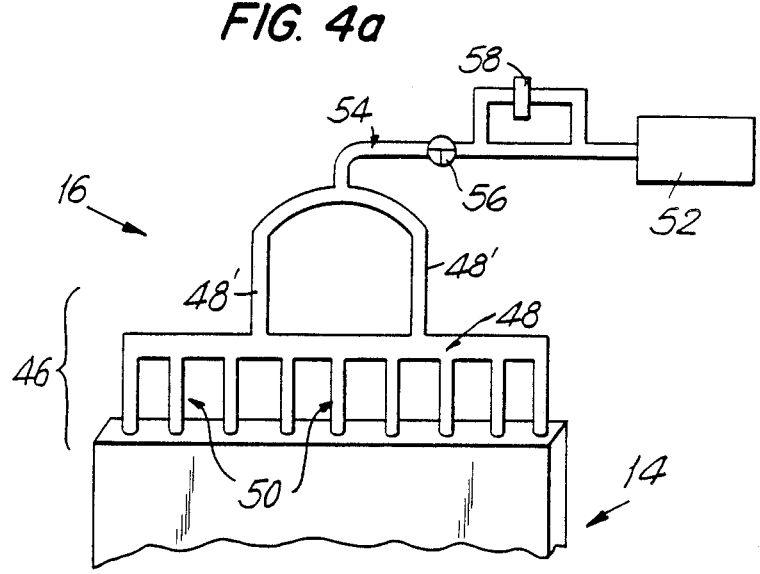
FIG. 4a is a schematic diagram of a preferred embodiment of the exhaust system of the apparatus of FIG. 1.

Hood assembly 14 includes an exhaust system 16 for evacuating the hood. FIG. 4a shows the preferred embodiment of exhaust system 16. The exhaust system produces a controlled rate of flow of the air and smoke within the hood. Exhaust system 16 includes an exhaust pipe assembly 46 mounted on top of hood assembly 14, having a manifold 48, connecting pipes 50, and a blower 52 connected to apply suction to manifold 48 and pipes 50.

Exhaust assembly 46 removes air and smoke from hood assembly 14 through one or more openings at the top of the hood. Exhaust assembly 46 is attached to hood assembly 14 at nine openings, which are spaced substantially evenly across the top portion of the hood. The exhaust system may be designed to draw slightly more air from the sides of the hood to compensate for boundary conditions. This design produces a substantially laminar flow of air within hood assembly 14, and minimizes turbulent air flow as the sidestream smoke is drawn past optical system 18. Achieving a substantially laminar flow within hood assembly 14 is important to ensure correct sensing of the light transmitted through the smoke. Turbulent air flow through the beam of light may cause the sidestream smoke to appear more concentrated than it actually is.

Figure 4B:
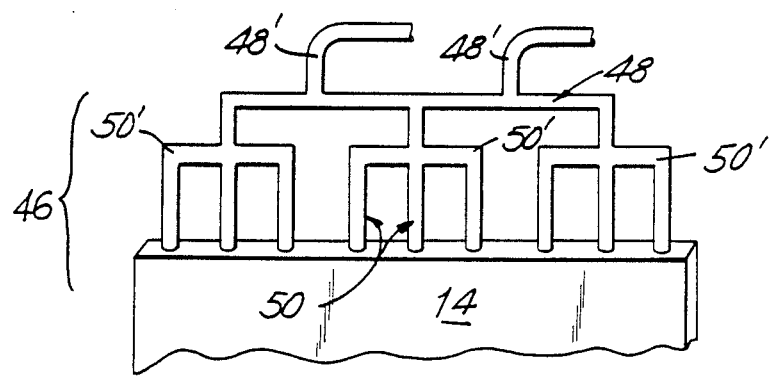
FIG. 4b is a schematic diagram of an alternative embodiment of the exhaust system of the apparatus of FIG. 1.

FIG. 4b shows an alternative embodiment of exhaust assembly 46, in which manifold 48 draws air and smoke from smaller manifolds 50'. Manifolds 50' draw air from hood assembly 14 by applying suction to connecting pipes 50.

Connecting pipes 50 exhaust into manifold 48, and the air and smoke are drawn from manifold 48 through pipes 48' and through a vacuum line 54 by blower 52. Blower 52 is commercially available from Gast Mfg. Corp., Benton Harbor, Michigan. The flow rate through vacuum line 54 may be controlled by a valve 56, and may be measured by a rotameter 58. The rotameter is isolated from the flow system in a bypass line during the sidestream smoke analyses, to prevent it from becoming contaminated by the smoke.

Figure 5:
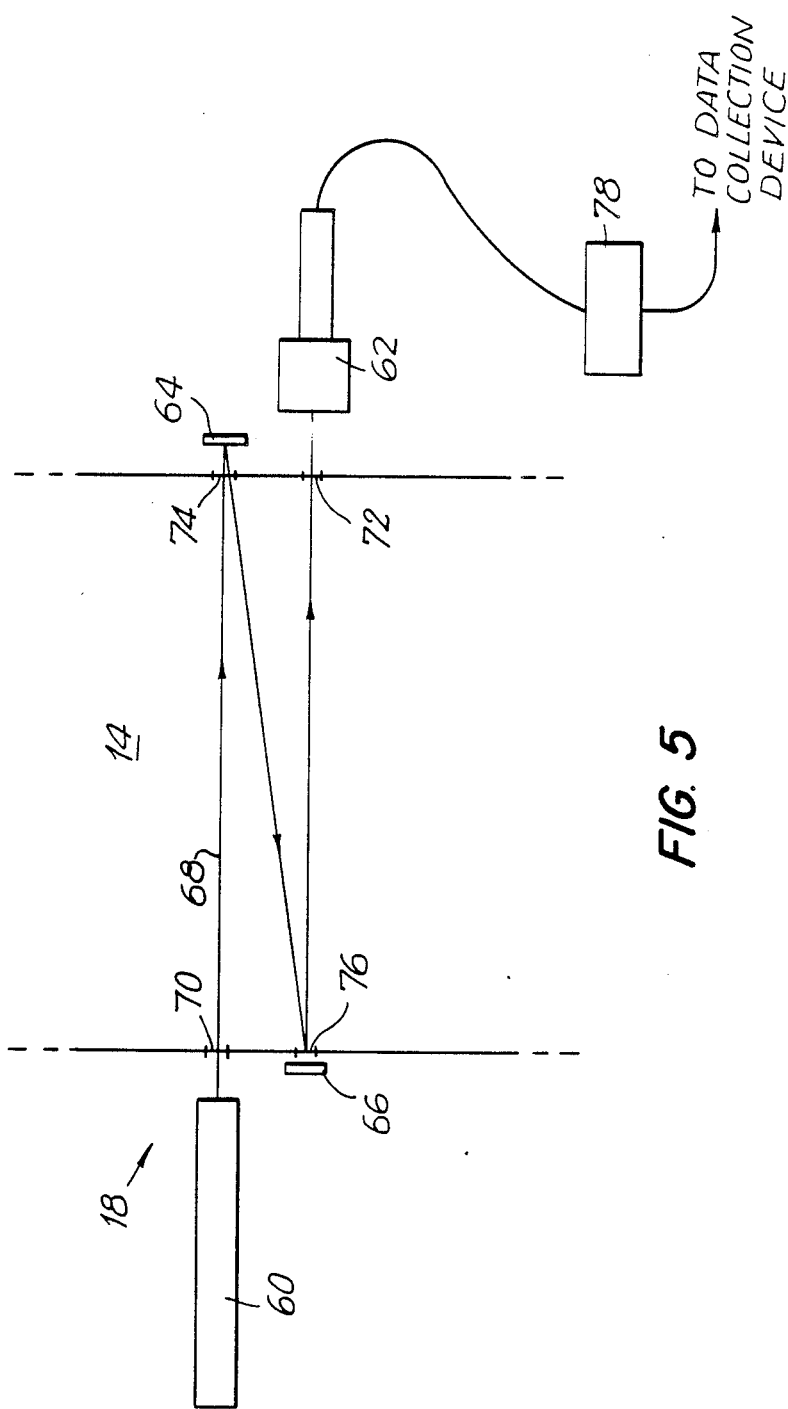
FIG. 5 is a schematic diagram of the optical system of the apparatus of FIG. 1.

Referring now to FIG. 5, optical system 18 for measuring the sidestream smoke includes illuminating source 60 and detector 62. The preferred embodiment of optical system 18 also includes mirrors 64 and 66 for effecting multiple passes of the light across hood assembly 14.

In the preferred embodiment, all of the components of optical system 18 are mounted exterior to hood assembly 14 to avoid errors caused by smoke deposition during testing. However, in an alternative embodiment one or more of the components may be contained within hood assembly 14.

Illuminating source 60 preferably is a green HeNe laser, having a wavelength of approximately 543.5 nm. A wavelength of 543.5 nm was selected because it is close to the maximum sensitivity of the human eye, which is about 555 nm. The laser offers the distinct advantage of producing a collimated beam of light, without using additional optics. Lasers suitable for this application are commercially available from PMS Electro-Optics, Boulder, Colorado. Alternatively, illuminating source 60 may be a non-laser light source. For example, illuminating source 60 may be a miniature xenon arc lamp or a quartz-halogen filament lamp. Both of these lamps produce an intense white light that can be used to emulate sunlight. Additional optics preferably are used to collimate the light output by these alternative light sources.

In another alternative embodiment, illuminating source 60 is a light source having a wavelength tuned to the absorption peaks of a compound whose concentration in the sidestream smoke is to be measured. For example, illuminating source 60 may be selected to measure the concentration of carbon dioxide in cigarette smoke. The wavelengths associated with the absorption peaks of these materials are commonly known in the art.

Detector 62 is a silicon photodiode detector (commercially available from Oriel Corp., Stratford, Connecticut). In the preferred embodiment, the laser beam 68 from illuminating source 60 is passed across the upper portion of the hood three times before its intensity is measured by detector 62. Laser beam 68 is projected to mirror 64, reflected back across hood assembly 14 to mirror 66, and then reflected to detector 62. The multiple passes are used to produce a path of sufficient length (e.g., 165 cm) to obtain a predetermined light transmission value (e.g., approximately 30 percent) for control cigarettes.

The transmission of laser beam 68 through the smoke preferably is measured at a distance of 45 cm above the cigarettes. This measuring height is not critical, and a range of heights may be selected. However, the measuring height should be selected to minimize the escape of volatile elements, and still permit the smoke to cool and form.

Windows are installed wherever laser beam 68 passes through the walls of hood assembly 14. Windows 70 and 72 are placed adjacent to illuminating source 60 and detector 62, respectively. Windows 74 and 76 are placed adjacent to mirrors 64 and 66, respectively, if multiple light passes are used. The use of windows permits all elements of optical system 18 to remain outside and independent of hood assembly 14. Suitable windows may be formed using microscope slide cover slips held in place with an adhesive, such as rubber cement. The windows are replaced when they become dirty from smoke deposition.

Detector 62 senses laser beam 68 and produces a signal—typically is the range of 0 to 50 mV—which is proportional to the light intensity sensed. The signal from detector 62 drives a readout unit 78 equipped with a digital meter and a sensitivity attenuator. The sensitivity attenuator permits any arbitrary light level to be displayed at 1.000, allowing direct transmission measurements (i.e., the sensitivity attenuator normalizes the received signal). A strip chart recorder may be connected to readout unit 78 to produce a hardcopy of the results of the sidestream smoke analyses.

Readout unit 78 preferably is connected to a computer system to facilitate the collection and processing of data. The computer system may be used together with a strip recorder, or either the computer system or strip recorder may be used alone. The computer system may be a personal computer equipped with a Data Translation board (commercially available from Data Translation, Inc., Marlboro, Massachusetts) and the LabTech Notebook program with a Real Time Access option (available from Laboratory Technologies, Corp., Wilmington, Massachusetts). The computer board and program permit the computer to receive the analog signal from the detector and convert it to a digital signal. The digital signal may then be stored and processed by the computer. A second computer program is used to facilitate collecting and processing the data. The listing of a program suitable for data collection and processing is provided in Appendix I. One skilled in the art could develop software for use with various operating systems.

Optical system 18 may be calibrated using commercially available neutral density filters. The filters are specified in terms of their optical density, defined as:

$$\text{Optical Density} = \log_{10}(1/T), \qquad [4] \text{ ps}$$

where T is the fraction of light transmitted through the filter. The neutral density filter calibrations at 550 nm are used for calculating the expected transmission values and adjusting the equipment accordingly. If a strip chart recorder is used, the zero and full scale positions of the recorder are adjusted before the calibration check is performed. The normal operating procedure used in actual sidestream smoke analyses (described below) is followed for each calibration check.

In addition to calibrating optical system 18, the delivery of cigarette smoke in the system must be checked. The flow of air through the hood should be great enough to capture all of the sidestream smoke, yet it should not be so great as to adversely affect the burning of the cigarettes. Any flow rate which accomplishes both of these objectives is acceptable. The following procedure may be used to set the flow rate. Standard test cigarettes with a known mainstream delivery (measured in total particulate matter, or "TPM") may be smoked in smoking machine 12 under dynamic conditions. The flow rate in hood assembly 14 is adjusted, using valve 56, until the mainstream delivery (TPM) of the standard test cigarettes match the expected delivery value. Although the flow rate may vary depending upon the dimensions of the hood assembly and other apparatus, a typical flow rate is approximately 96 liters/minute.

The following procedure may be used to perform continuous, static sidestream smoke analyses. During static testing, the test cigarettes are not puffed with smoking machine 12 after the initial lighting puff. The cigarettes to be tested in system 10 are marked at starting and ending points for the analyses at predetermined distances (e.g., 15 mm and 45 mm, respectively) from the lighting end. A third mark is made about 9 mm from the butt end of the test cigarette. Eight such cigarettes are inserted, to the 9 mm mark, in smoking ports 20 of smoking machine 12. The flow rate of the hood is adjusted if necessary. The test cigarettes are then lit, preferably using a lighting bar. Only a lighting puff is taken; smoking machine 12 is turned off after the lighting puff. The cigarettes under test are permitted to burn and to generate sidestream smoke. The sides and front of the hood are closed. Computer data collection is started when the char line of the burning cigarette reaches the predetermined starting point. Voltage levels from detector 62 preferably are recorded at a rate of 4 per second, but this rate may be increased or decreased for a particular application. Data collection is halted when the char line reaches the predetermined ending point.

Continuous, dynamic sidestream smoke analyses may also be performed in accordance with the present invention. The apparatus is set up in the same manner as for performing static testing. However, after lighting, the test cigarettes are puffed by smoking machine 12 during the analyses. The cigarettes under test are puffed for two seconds with a 35 cubic centimeter puff, and are permitted to burn, without puffing, for an additional 58 seconds. The mainstream smoke (i.e., smoke drawn through the article during puffing) is separated from the sidestream smoke and discharged exterior to hood assembly 14, into the atmosphere. The sequence is repeated until the cigarettes have burned to the predetermined ending point. As with static testing, smoke is not accumulated in hood assembly 14 during dynamic testing. Smoke is continuously drawn past optical system 18 by exhaust system 16. Dynamic testing permits an analysis of variations in the amount of sidestream smoke produced when a cigarette is puffed. This analysis is not possible using a method in which smoke is accumulated within hood assembly 14.

Thus a system for continuously monitoring and quantitatively measuring sidestream smoke from cigarettes is provided. One skilled in the art will appreciate that the present invention can be practiced by other than the described embodiments, which are presented here for purposes of illustration and not of limitation, and the present invention is limited only by the claims that follow.

What is claimed is:

1. Apparatus for measuring the relative amount of sidestream smoke produced by a burning smoking article comprising:
    means for holding the smoking article and burning the same;
    means including a chamber surrounding said burning article for receiving sidestream smoke therefrom;
    a hood assembly in fluid communication with said chamber;
    means for drawing sidestream smoke through said chamber and through said hood assembly and to discharge said sidestream smoke externally of said hood assembly at a substantially constant rate which prevents accumulation of sidestream smoke in said hood assembly;
    means for transmitting a beam of light having a predetermined intensity across the hood assembly and through the sidestream smoke passing therethrough; and
    means for detecting and measuring the intensity of said beam of light after passage through said sidestream smoke as an indication of the concentration of sidestream smoke.

2. The apparatus of claim 1 wherein the reflecting means includes at least one mirror mounted in the path of the beam of light for passing said beam through the sidestream smoke more than once before the intensity of said beam is detected.

3. The apparatus of claim 1 wherein the means for transmitting a beam of light is a laser.

4. The apparatus of claim 3 wherein the laser emits light having a wavelenth in the range of about 535 nm to about 565 nm.

5. The apparatus of claim 1 wherein the holding means is a smoking machine capable of drawing a predetermined quantity of air through the burning smoking article at predetermined intervals and includes means to discharge the air drawn through said article outside of said chamber.

6. The apparatus of claim 1 wherein said chamber is provided with an opening through which outside air is drawn into said chamber and thence into said hood assembly through action of said drawing means.

7. The apparatus of claim 1 wherein the drawing means includes a manifold which draws substantially evenly from each of a plurality of ports at the top of said hood assembly to produce a substantially laminar flow of sidestream smoke within the hood assembly.

8. The apparatus of claim 1 wherein the detecting means is a photodiode detector which produces a voltage that is proportional to the intensity of the beam of light.

9. The apparatus of claim 1, further comprising data collection means.

10. Apparatus for measuring the relative amount of sidestream smoke produced by a burning smoking article comprising:
    means including a chamber surrounding said burning article for receiving sidestream smoke therefrom;
    a smoking machine capable of drawing a predetermined quantity of air through the burning smoking article at predetermined intervals and including means to discharge the air drawn through said article outside of said chamber, said smoking machine also being capable selectively of allowing the burning article to smolder without drawing air therethrough thereby to simulate a smoking article smoldering in a receptacle;
    a hood assembly in fluid communication with said chamber;
    means for drawing the sidestream smoke from said chamber and through said hood assembly and to discharge said sidestream smoke externally of said hood assembly at a substantially constant rate which prevents accumulation of sidestream smoke in said hood assembly;
    a laser for transmitting a beam of light across the hood assembly and through the sidestream smoke passing therethrough;
    a photodiode detector which produces a voltage that is proportional to the intensity of the beam of light after passage through said sidestream smoke as an indication of the concentration of sidestream smoke; and
    a plurality of mirrors mounted in the path of the beam of light for causing multiple passes of said beam through the sidestream smoke before the intensity of said beam is detected.

11. A method for continuously and instantaneously measuring the amount of light transmitted through sidestream smoke produced by a smoking article comprising the steps of:
    burning the smoking article to produce sidestream smoke and mainstream smoke;
    maintaining separate said sidestream smoke and said mainstream smoke and discharging the latter to the outside atmosphere;
    drawing the sidestream smoke through a chamber at a relatively constant rate which prevents accumulation of said sidestream smoke in said chamber;
    passing a beam of light having a predetermined intensity through said sidestream smoke as the smoke is being passed through said chamber; and detecting and measuring the intensity of the beam of light after it has passed through the sidestream smoke.

12. The method of claim 11 comprising the additional step of calculating the extinction coefficient of the sidestream smoke.

13. The method of claim 11 wherein said sidestream smoke is caused to exit from said chamber through a plurality of spaced ports to inhibit turbulent flow in said chamber.

14. The method of claim 11 wherein the step of burning the smoking article comprises:
  lighting the smoking article; and
  permitting the smoking article to burn substantially without drawing air through the article to simulate the condition in which a smoking article is left burning in a receptacle.

15. The method of claim 11 wherein the step of burning the smoking article comprises:
  lighting the smoking article; and
  drawing air through the smoking article at predetermined intervals to simulate the function and operation of the article in normal smoking.

16. The method of claim 11 wherein the step of detecting the intensity of the light beam transmitted through the sidestream smoke comprises:
  detecting the intensity of the light beam with a photodiode detector; and
  producing a voltage that is proportional to the intensity of the light beam.

17. The method of claim 11 wherein the beam of light has a wavelength which corresponds to a known absorption peak of a compound in the sidestream smoke produced by the smoking article.

* * * * *